(12) United States Patent
Bistrian et al.

(10) Patent No.: US 9,034,917 B2
(45) Date of Patent: May 19, 2015

(54) SN-2-MONOACYLGLYCEROLS AND LIPID MALABSORPTION

(71) Applicant: Nestec S.A., Vevey (CH)

(72) Inventors: Bruce Bistrian, Ipswich, MA (US); Frederic Destaillats, Servion (CH); Cristina Cruz-Hernandez, Epalinges (CH); Fabiola Dionisi, Epalinges (CH); Isabelle Masserey-Elmelegy, Epalinges (CH); Manuel Oliveira, Chexbres (CH); Julie Celine Moulin, Attalens (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/163,163

(22) Filed: Jan. 24, 2014

(65) Prior Publication Data

US 2014/0142169 A1  May 22, 2014

Related U.S. Application Data

(62) Division of application No. 13/808,779, filed as application No. PCT/EP2011/061265 on Jul. 5, 2011, now abandoned.

(30) Foreign Application Priority Data

Jul. 5, 2010  (EP) ..................................... 10168420

(51) Int. Cl.
    *A01N 43/02* (2006.01)
    *A61K 31/335* (2006.01)
    *A61K 31/232* (2006.01)
    *A23L 1/30* (2006.01)
    *A61K 31/202* (2006.01)
    *A61K 31/357* (2006.01)

(52) U.S. Cl.
    CPC .............. *A61K 31/232* (2013.01); *A23L 1/3006* (2013.01); *A23L 1/3008* (2013.01); *A23V 2002/00* (2013.01); *A61K 31/202* (2013.01); *A61K 31/357* (2013.01)

(58) Field of Classification Search
    None
    See application file for complete search history.

(56) References Cited

U.S. PATENT DOCUMENTS

| 7,097,674 B2 | 8/2006 | Delfort et al. |
| 2005/0281864 A1 | 12/2005 | Turini et al. |
| 2008/0275120 A1 | 11/2008 | Peters et al. |

FOREIGN PATENT DOCUMENTS

EP  1704861  9/2006

OTHER PUBLICATIONS

Magnusson et al. "Chemoenzymatic synthesis of symmetrically structured triacylglycerols possessing short-chain fatty acids" Feb. 4, 2010, Tetrahedron, 66, pp. 2728-2731.
Del Mar Munio et al. "Synthesis of 2-monoacylglycerols rich in polyunsaturated fatty acids by ethanolysis of fish oil catalyzed by 1,3 specific lipases" Process Biochemistry, 43 (2008), pp. 1033-1039, XP002544267.
Bayon et al. "Two step synthesis of 1,3-acetylated, -butyroylated and -caproylated triglycerides from a microorganism oil rich in Docosahexaenoic Acid (DHA)" Bioorganic & Medicinal Chemistry Letters, vol. 6, No. 4, pp. 345-348, 1996, XP004135033.
Guillon et al. "First Total Synthesis of 1,3-Diacetyl- and -Dibutyroyl-2-oleoylglycerol, Previously Isolated From Natural Products" Pharmacy and Pharmacology Communications, vol. 5, No. 5, 1999, pp. 311-313, XP008112959.
Christensen et al. "Intestinal absorption and lymphatic transport of eicosapentaenoic (EPA), docosahexaenoic (DHA), and decanoic acids: dependence on intramolecular triacylglycerol structure" Am. J. Clin. Nutr., 1995, 61, pp. 56-61, XP002600055.

*Primary Examiner* — Dennis Heyer
*Assistant Examiner* — Daniel M Podgorski
(74) *Attorney, Agent, or Firm* — K&L Gates LLP

(57) ABSTRACT

The present invention relates generally to the field of lipids and in particular aims at improving lipid absorption, for example under conditions of lipid maldigestion or malabsorption. One embodiment of the present invention relates to a composition comprising a sn-2 monoacylglycerol derivative, wherein the sn-1 and sn-3 positions are blocked by protective groups. The acyl group may be a fatty acid, for example one with anti-inflammatory properties.

5 Claims, 2 Drawing Sheets

A                    B

SN-2-MONOACYLGLYCEROLS AND LIPID MALABSORPTION

PRIORITY CLAIM

Figure 1:
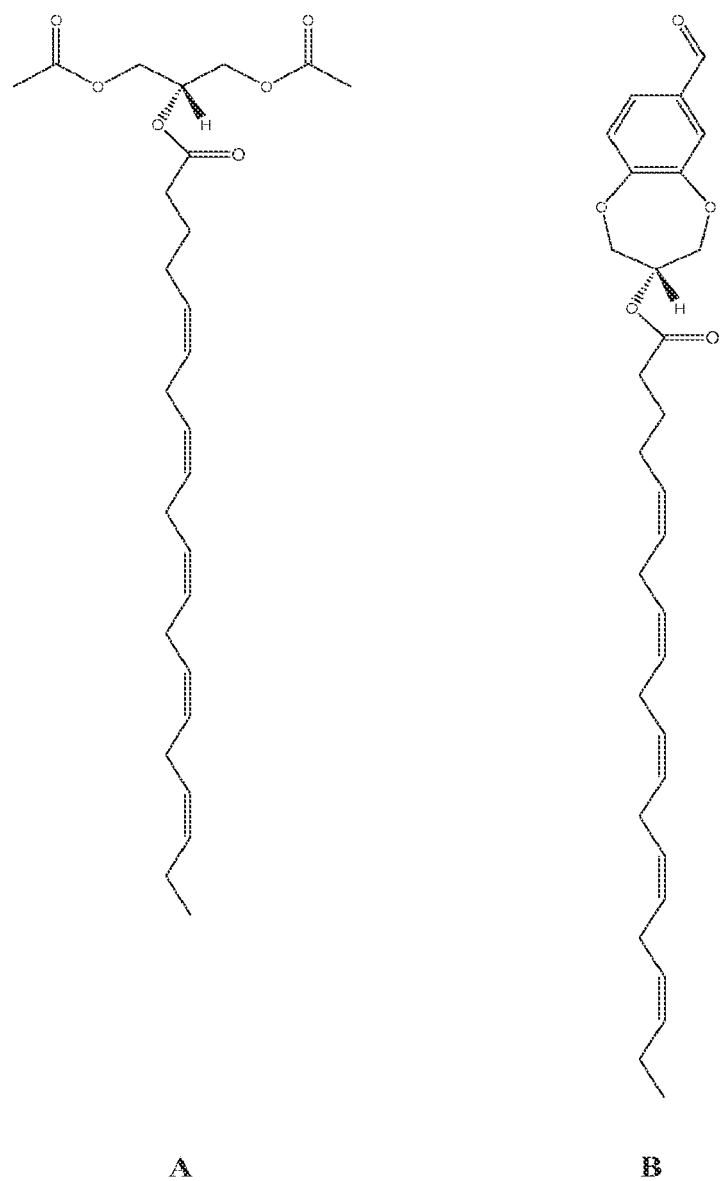

This application is a divisional application of U.S. patent application Ser. No. 13/808,779, filed on Jan. 7, 2013, which is a National Stage of International Application No. PCT/EP2011/061265, filed Jul. 5, 2011, which claims priority to European Application No. 10168420.7, filed Jul. 5, 2010, the entire contents of which are being incorporated herein by reference.

BACKGROUND

The present invention relates generally to the field of lipids and in particular aims at improving lipid absorption, for example under conditions of lipid malabsorption. One embodiment of the present invention relates to a composition comprising an sn-2 monoacylglycerol derivative, wherein the sn-1 and sn-3 positions are blocked by protective groups. The acyl group may be a fatty acid, for example one with anti-inflammatory properties.

The delivery of bioactive fatty acids under conditions of malabsorption such as in pancreatic insufficiency, bile salt deficiency, short gut due to gut removal or mucosal disease is critical.

In these physiological conditions, the digestion pathways, involving degradation of dietary triacylglycerols by the pancreatic lipase and the formation of micellar macrostructures required for enteral uptake, are impaired.

The delivery of bioactive fatty acids having, e.g., anti-inflammatory properties is therefore critical in these conditions as this type of fatty acids could help to lower the inflammation response.

Based on previously published prior art (Mattson F. H. and Volpenhein R. A. (1964); Hunter E. J. (2001); Hayes K. C. (2001)) one might assume that fatty acids located in the sn-2 position of a glyceride are more readily absorbed by the body than fatty acids in the sn-1 or sn-3 position.

However, for example in monoacylglycerols (MAGs) it is known that unsaturated Sn2-MAGs tend to isomerise with storage time and/or increased temperatures when preparing a meal, for example, to yield a significant amount of sn-1 and sn-3 MAGs, which are less readily absorbed.

A food composition prepared with only sn-2 MAGs to improve lipid absorption would, hence, lose its benefit with time.

For humans, there is presently no dietary solution available to deliver essential fatty acids, in particular when mechanisms involved in lipid digestion and absorption are impaired. Hence, in hospitals parenteral nutrition formulations are used.

In aged companion animals, such as old dogs or cats for example, there is equally no solution available as well.

However, it would be desired to have a food composition available that allows the efficient uptake of fatty acids even under conditions of lipid malabsorption.

SUMMARY

Hence, it was the objective of the present invention to provide the art with an optimal glyceride structure allowing a substantial uptake of fatty acids, for example fatty acids with anti-inflammatory properties, such as EPA, in particular in malabsorption conditions.

The inventors were surprised to see that they could achieve this objective by the subject matter of the independent claim. The dependent claims define further embodiments of the present invention.

DETAILED DESCRIPTION OF THE DRAWINGS

FIG. 1 shows examples of EPA glycerides used in the present invention: (A) 1,3-diacetyl-2-eicosapentaenoylglycerol and (B) an acetal derivative of sn-2 monoeicosapentaenoylglycerol.

Figure 2:
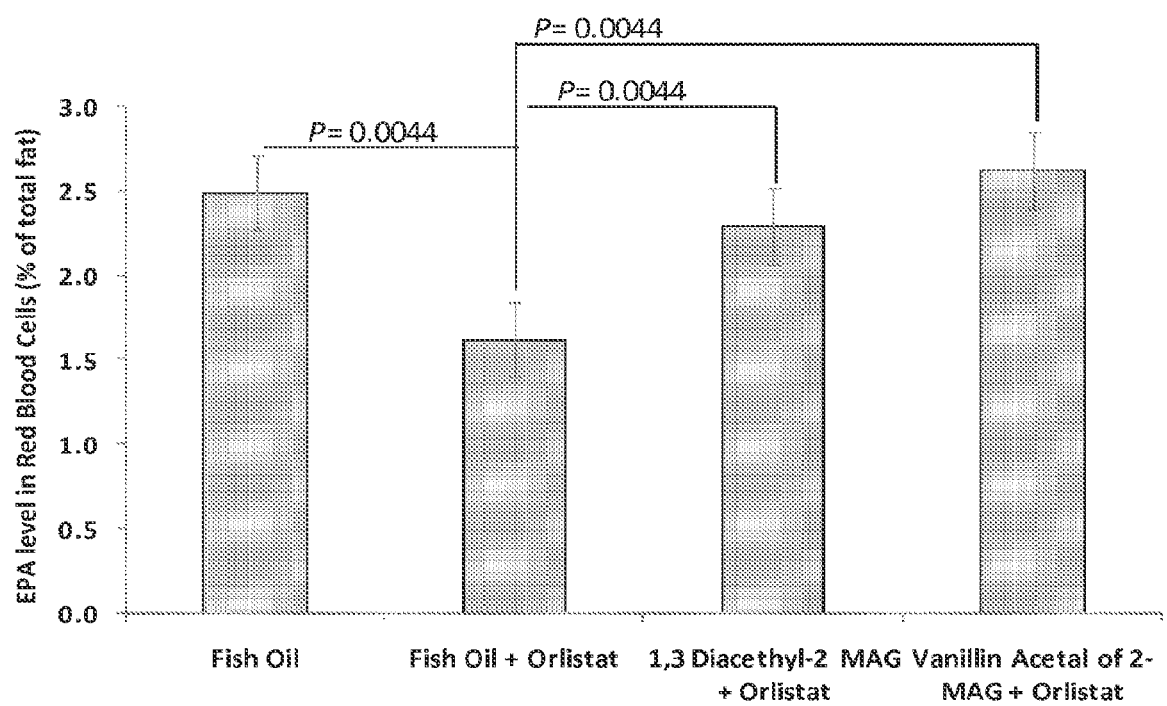

FIG. 2 shows the incorporation of EPA in red blood cells. Treatments: Control rats fed fish oil with or without Orlistat and rats fed NAG derivatives (A and B) described in FIG. 1. Values are means±SEM (n=6).

DETAILED DESCRIPTION

The inventors found that they could significantly improve fatty acid absorption by using sn-2 monoacylglycerol derivatives, wherein the sn-1 and sn-3 positions are blocked by protective groups.

Without wishing to be bound by theory the inventors presently believe that by blocking the sn-1 and sn-3 position of a Sn-2 MAGs the isomerisation can be avoided and 100% of the better absorbed sn-2 MAGs can be provided. Importantly, this improved absorbability persists with storage times and withstands temperature increases.

Hence, the present invention is related to the use of sn-2 MAGs and MAG derivatives (see FIG. 1) to deliver bioactive fatty acids such as eicosapentaenoic acid (EPA), e.g., under lipid malabsorption conditions.

MAGs do not need to be digested prior to absorption and have intrinsic emulsifying properties allowing a good dispersion of oil droplets prior to absorption in the intestine. Further, MAGs are better absorbed than free fatty acids.

The inventors tested their concept in a lipid malabsorption animal model. The lipid maldigestion/malabsorption conditions were obtained using Orlistat®, a well known pancreatic and gastric lipases inhibitor. Animals were fed with long-chain polyunsaturated fatty acid (LC-PUFA) supplements containing mainly eicosapentaenoic (EPA) acid. Fish oil was used as a source of triacylglycerols and different EPA glycerides, for example those of FIG. 1, were evaluated. At different time intervals the fatty acid profile of red blood cells and plasma lipids was assessed. At the end of the experiment, fatty acid profiles of different tissues were determined. A statistical evaluation revealed that the use of Orlistat® decreases EPA incorporation in red blood cells. The level of, e.g., EPA incorporated in red blood cells in an animal receiving the MAG derivatives of the present invention was found to be significantly higher compared to the administration of fish oil with mixture of EPA in sn-1, sn-2 and sn-3 positions. This clearly demonstrates that, e.g., in conditions of lipid malabsorption, the incorporation of LC-PUFA provided as triacylglycerols is reduced. However, if LC-PUFA are provided as NAG derivatives of the present invention the incorporation in tissue is not altered in conditions of lipid malabsorption.

Hence, one embodiment of the present invention is a composition comprising an sn-2 monoacylglycerol derivative, wherein the sn-1 and sn-3 positions are blocked by protective groups.

The acyl group may be any fatty acid, for example.

The composition of the present invention may be used to provide at least one essential fatty acid in order to prevent essential fatty acid deficiency, or to provide at least one distal fatty acid, such as arachidonic, eicosapentaenoic, or docosahexaenoic acid in conditions where elongation and desaturation of linoleic or alpha linolenic acid are impaired.

This may be the case in pre-term infants or patients with severe liver insufficiency, for example.

The acyl group may be a fatty acid with anti-inflammatory properties. Which fatty acids have anti-inflammatory properties is known to those of skill in the art.

For example, fatty acids having anti-inflammatory properties may be selected from the group consisting of eicosapentaenoic acid (EPA), docosahexaenoic acid (DHA), α-linolenic acid (ALA), stearidonic acid (SA), γ-linolenic acid (GLA), dihomo-γ-linolenic acid (DGLA), n-3 docosapentanenoic acid (DPA), sciadonic acid and juniperonic acid.

Of course, the composition may comprise a mixture of different MAGs with different fatty acids in sn-2 position and/or with different protective groups in sn-1 and/or sn-3 position.

The fatty acids may be mixed in a way, for example, that a particular ratio between n-3 and n-6 fatty acids is used.

n-3 Fatty acids include for example α-linolenic acid, stearidonic acid, n-3 eicosatrienoic acid, n-3 eicosatetraenoic acid, eicosapentaenoic acid, clupanodonic acid, docosahexaenoic acid, n-3 tetracosapentaenoic acid.

n-6 Fatty acids include for example linoleic acid, γ-linolenic acid, n-6 eicosadienoic acid, dihomo-γ-linolenic acid, arachidonic acid, n-6 docosadienoic acid, adrenic acid, n-6 docosapentaenoic acid (Osbond acid).

Alternatively, conjugated fatty acids such as rumenic or calendic, catalpic or eleostearic acids or nonmethylene-interrupted Δ5-polyenoic (NMIP) fatty acids such as taxoleic, pinolenic, sciadonic or juniperonic acids can be mixed in a way to sn-2 MAG derivatives.

The composition may contain a combination of different sn-2 MAG derivatives; for example with a ratio of n-3 to n-6 fatty acids of about 5:1 to about 15:1; for example about 8:1 to about 10:1.

Any protective groups that are acceptable for food products may be used. Those skilled in the art will be able to identify appropriate protective groups easily.

Ideally, such protective groups should be tasteless or have a taste that is generally perceived as pleasant.

For example, the protective groups may be selected from the group consisting of acetyl groups, ethyl groups, propyl groups, vanillin, or other molecules able to form acetals.

For some applications it may be preferable, if a protective group is selected that is able to bridge the hydroxyl groups in sn-1 and sn-3 position.

Such a bridging effect will be advantageous when preparing the MAG derivative, as these two binding sites will produce a thermodynamic advantage compared to the association with only one hydroxyl group. For steric reasons, there will also be hardly any molecule where the protective group accidentally binds to sn-1(3) and sn-2 instead of sn-1 and sn-3.

Many combinations of fatty acids and protective groups may be selected based on the intended benefit to be delivered and the nature of the final composition. All these combinations are comprised by the present invention.

For example, the sn-2 monoacylglycerol derivative may be selected from the group consisting of
- 1,3-diacetyl-2-eicosapentaenoylglycerol,
- 1,3-diethyl-2-eicosapentaenoylglycerol,
- 1,3-dipropyl-2-eicosapentaenoylglycerol,
- a vanillin derivative of sn-2 monoeicosapentaenoylglycerol,
- other acetal derivatives of monoeicosapentaenoylglycerol, or combinations thereof.

The composition of the present invention may be any kind of edible composition. A composition is considered "edible" if it is approved for human or animal consumption.

Preferably, the composition is a composition to be administered orally or enterally.

For example, the composition may be selected from the group consisting of a food product, an animal food product, a pharmaceutical composition, a nutritional composition, a nutraceutical, a drink, a food additive or a medicament.

For example, the composition may be a liquid nutritional formula to be administered enterally, e.g., in hospitals.

The composition may also be a nutritional formulation to be administered to people above the age of 60.

The composition may also be a powdered composition to be reconstituted in milk or water.

If the composition is provided in the form of a powder, it may be a shelf stable powder. Shelf stability can be obtained, for example by providing the composition with a water activity smaller than 0.2, for example in the range of 0.19-0.05, preferably smaller than 0.15. Water activity or $a_w$ is a measurement of the energy status of the water in a system. It is defined as the vapor pressure of water divided by that of pure water at the same temperature; therefore, pure distilled water has a water activity of exactly one.

The caloric density of the composition of the present invention may be adjusted to the needs of the patient.

For example, the composition in accordance with the present invention may have a caloric density in the range of 0.5 kcal/ml to 15 kcal/ml.

For patients suffering from malabsorption and/or low appetite rather high caloric densities may be preferred. For such patients caloric densities in the range of 7-12 kcal/ml may be used.

The composition may also contain a protein source and/or a carbohydrate source. Easily digestible carbohydrates and/or proteins are preferred.

At least partially hydrolysed proteins are easier to digest and absorb. Hence, it may be desirable to supply at least partially hydrolysed proteins (degree of hydrolysis between 2 and 20%). If hydrolysed proteins are required, the hydrolysis process may be carried out as desired and as is known in the art. For example, a protein hydrolysate may be prepared by enzymatically hydrolysing a protein fraction in one or more steps. For an extensively hydrolysed protein, the proteins may be subjected to triple hydrolysis using Alcalase 2.4 L (EC 940459), then Neutrase 0.5 L (obtainable from Novo Nordisk Ferment AG) and then pancreatin at 55° C.

The amount of fatty acids in the composition of the present invention may be adjusted to the patients needs.

In therapeutic applications, the MAG derivatives are administered in an amount sufficient to at least partially cure or arrest the symptoms of the disease and its complications. An amount adequate to accomplish this is defined as "a therapeutically effective dose". Amounts effective for this purpose will depend on a number of factors known to those of skill in the art such as the severity of the disease and the weight and general state of the patient.

In prophylactic applications, MAG derivatives are administered to a patient susceptible to or otherwise at risk of a particular disease in an amount that is sufficient to at least partially reduce the risk of developing a disease. Such an amount is defined to be "a prophylactic effective dose". Again, the precise amounts depend on a number of patient specific factors such as the patient's state of health and weight.

The compositions of the present invention are to be administered in an amount sufficient to provide the MAG derivatives in a therapeutically effective dose or a prophylactic effective dose.

For example, the composition may comprise the sn-2 MAG derivatives in an amount corresponding to about 3% to 40% of the energy of the composition. As low as 3% of arachidonic acid, eicosapentaenoic acid, and/or docosahexaenoic acid may meet essential fatty acid needs as well as provide effective anti-inflammatory effects. The composition of the present invention may be for use in the delivery of functional fatty acids.

Functional fatty are for the purpose of the present invention fatty acids that deliver a health benefit.

For example, composition of the present invention may be for use in the delivery of fatty acids having anti-inflammatory properties.

The composition of the present invention is in particular useful under conditions of lipid maldigestion or malabsorption.

Consequently, the composition of the present invention may be to be administered to subjects suffering from a lipid maldigestion or malabsorption condition.

The composition is useful for subject suffering from any kind of lipid maldigestion or malabsorption condition. For example, such a malabsorption condition may be due to pancreatic insufficiency, bile salt deficiency, a mucosal disorder and/or a short gut.

For example, if the fatty acid comprised by the MAG derivative is a fatty acid having anti-inflammatory properties, the composition in accordance with the present invention may be for use in the treatment or prevention of inflammatory disorders.

The present invention also relates to the use of a sn-2 MAG derivative, wherein the sn-1 and sn-3 positions are blocked by protective groups and wherein the acyl group is a fatty acid having anti-inflammatory properties for the preparation of a composition to treat or prevent inflammatory disorders, in particular under lipid maldigestion and/or malabsorption conditions.

The inflammatory disorder may be selected from the group consisting of acute inflammations such as sepsis, and chronic inflammations such as inflammatory bowel disease, Crohn's disease, ulcerative colitis, necrotizing enterocolitis, skin inflammation, such as UV or chemical-induced skin inflammation, eczema, reactive skin, psoriasis, vitiligo, acne, inflammatory bowel syndrome, liver inflammation, alcoholic cirrhosis, allergy, atopy, bone inflammation, rheumatoid arthritis, systemic lupus, dermato-myositis, thyroiditis, type I diabetes, celiac disease, Biermer's disease, multiple sclerosis, encephalomyelitis, eye inflammation, obesity-associated inflammation, age-related low-grade inflammation, Blau's syndrome, Alzheimer's disease, cardiovascular diseases, atherosclerosis, metabolic syndrome, or combinations thereof.

Those skilled in the art will understand that they can freely combine all features of the present invention described herein, without departing from the scope of the invention as disclosed. In particular, features described for the uses of the present invention may be applied to the compositions of the present invention and vice versa.

Further advantages and features of the present invention are apparent from the following Examples and Figures.

EXAMPLES

The concept was tested in a lipid maldigestion or malabsorption animal model. The maldigestion or malabsorption condition was obtained using Orlistat, a well known pancreatic and gastric lipases inhibitor. Animals were fed during 21 days with long-chain polyunsaturated fatty acid (LC-PUFAs) supplements containing mainly eicosapentaenoic (EPA) acid. Fish oil was used as a source of triacylglycerols and the different EPA glycerides provided in FIG. 1 were evaluated. Orlistat was given at a level sufficient to decrease lipid absorption by 40%. A group receiving fish oil without Orlistat was used as a positive control. At different time intervals (D-3, D7, D14 and D21), fatty acid profile of red blood cells and plasma lipids were performed. At the end of the experiment, fatty acid profiles of different tissues were determined.

The main objective was to follow the level of EPA in red blood cell and plasma lipids. The main comparison evaluated was the difference in EPA level between groups receiving EPA derivatives (FIG. 1) in combination with Orlistat and the positive control group (fish oil+Orlistat).

As an example, data obtained for EPA levels in red blood cells lipids at day 7 are reported in FIG. 2. The statistical evaluation revealed that the use of Orlistat decrease EPA incorporation in red blood cells (comparison between the group receiving fish oil in combination or not with Orlistat). This comparison is very important since it validates the validity of the model. The level of EPA incorporated in red blood cells in animal receiving the MAG derivatives is statistically higher that the fish oil+Orlistat group (all P values lower that 0.05).

This example clearly demonstrates that in condition of lipid maldigestion or malabsorption, the incorporation of LC-PUFA provided as triacylglycerols is reduced. However, if LC-PUFA are provided as MAG derivatives (group A and B), the incorporation in tissue is not altered, even in conditions of lipid maldigestion or malabsorption.

The invention is claimed as follows:

1. A method for delivering fatty acids to an individual having lipid maldigestion or malabsorption condition, the method comprising:
    administering a composition comprising an sn-2 monoacylglycerol, wherein the sn-1 and sn-3 positions are blocked by protective groups and the acyl group is a fatty acid having anti-inflammatory properties selected from the group consisting of eicosapentaenoic acid (EPA), docosahexaenoic acid (DHA), α-linolenic acid (ALA), stearidonic acid (SA), γ-linolenic acid (GLA), dihomo-γ-linolenic acid (DGLA), n-3 docosapentanenoic acid (DPA), sciadonic acid and juniperonic acid, to an individual in need of same.

2. The method in accordance with claim 1, wherein the maldigestion or malabsorption condition is due to pancreatic insufficiency, bile salt deficiency and/or a short gut.

3. The method in accordance with claim 1, wherein the protective groups are selected from the group consisting of acetyl groups, ethyl groups, propyl groups, vanillin, and other molecules able to form acetals.

4. A method for the treatment of lipid maldigestion or malabsorption conditions selected from the group consisting of pancreatic insufficiency, bile salt deficiency, and/or a short gut, the method comprising:
    administering a composition comprising a sn-2 monoacylglycerol, wherein the sn-1 and sn-3 positions are blocked by protective groups and the acyl group is a fatty acid having anti-inflammatory properties selected from the group consisting of eicosapentaenoic acid (EPA), docosahexaenoic acid (DHA), α-linolenic acid (ALA), stearidonic acid (SA), γ-linolenic acid (GLA), dihomo- γ-linolenic acid (DGLA), n-3 docosapentanenoic acid (DPA), sciadonic acid and juniperonic acid, to an individual in need of same.

5. The method in accordance with claim 4 wherein the individual is a pre-term infant.

\* \* \* \* \*